(12) United States Patent
Colvin et al.

(10) Patent No.: US 9,532,886 B2
(45) Date of Patent: Jan. 3, 2017

(54) ADDITIVE MANUFACTURING PRODUCED PROSTHETIC FOOT

(71) Applicant: The Ohio Willow Wood Company, Mount Sterling, OH (US)

(72) Inventors: James M. Colvin, Hilliard, OH (US); Jeffrey A. Denune, Galloway, OH (US); James W. Capper, Washington Court House, OH (US); Michael L. Haynes, Columbus, OH (US)

(73) Assignee: THE OHIO WILLOW WOOD COMPANY, Mt. Sterling, OH (US)

( * ) Notice: Subject to any disclaimer, the term of this patent is extended or adjusted under 35 U.S.C. 154(b) by 0 days.

(21) Appl. No.: 14/976,703

(22) Filed: Dec. 21, 2015

(65) Prior Publication Data

US 2016/0106555 A1  Apr. 21, 2016

Related U.S. Application Data (62) Division of application No. 14/214,842, filed on Mar. 15, 2014, now abandoned.
(Continued)

(51) Int. Cl.
*A61F 2/50* (2006.01)
*A61F 2/66* (2006.01)
*A61F 2/60* (2006.01)

(52) U.S. Cl.
CPC ............... *A61F 2/66* (2013.01); *A61F 2/5044* (2013.01); *A61F 2002/5001* (2013.01);
(Continued)

(58) Field of Classification Search
CPC .............. A61F 2/60; A61F 2/601; A61F 2/66; A61F 2/6607; A61F 2/76; A61F 2002/5003; A61F 2002/5009; A61F 2002/503;A61F 2002/5075; A61F 2002/5072; A61F 2002/5073; A61F 2002/5078; A61F 2002/6614; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692

See application file for complete search history.

(56) References Cited

U.S. PATENT DOCUMENTS 6,120,547 A * 9/2000 Christensen ............... A61F 2/66
                                                      623/38
6,666,895 B2 * 12/2003 Johnson ................ A61F 2/5046
                                                      623/47
(Continued)

FOREIGN PATENT DOCUMENTS

FR          2626463 A1 *  8/1989   ............... A61F 2/66

OTHER PUBLICATIONS

Translation of FR2626463A1. Espacenet Translation.*

*Primary Examiner* — Thomas J Sweet
*Assistant Examiner* — Christie Bahena
(74) *Attorney, Agent, or Firm* — Benesch, Friedlander, Coplan & Aronoff LLP (57) ABSTRACT

A prosthetic foot structure includes a primary foot member and a heel member. The primary foot member has a heel portion, a toe portion with a pair of toe sections separated by a gap, and an elongated intermediate portion configured as an arch extending downward from the heel portion toward the toe portion. The heel member includes a hollow cylindrical spring wall extending downward from the heel portion of the primary foot member. The primary foot member and (Continued)

the heel member are portions of a unitary body of material formed by additive manufacturing.

3 Claims, 8 Drawing Sheets

Related U.S. Application Data (60) Provisional application No. 61/801,118, filed on Mar. 15, 2013.

(52) U.S. Cl.
CPC . *A61F 2002/5007* (2013.01); *A61F 2002/607* (2013.01); *A61F 2002/6621* (2013.01)

(56) References Cited

U.S. PATENT DOCUMENTS

| | | | | |
|---|---|---|---|---|
| 2002/0013628 A1* | 1/2002 | Harris | A61F 2/66 | 623/55 |
| 2002/0177906 A1* | 11/2002 | Phillips | A61F 2/60 | 623/27 |
| 2004/0215346 A1* | 10/2004 | Rubie | A61F 2/66 | 623/38 |
| 2004/0225376 A1* | 11/2004 | Townsend | A61F 2/66 | 623/52 |
| 2005/0267603 A1* | 12/2005 | Lecomte | A61F 2/66 | 623/52 |
| 2008/0004719 A1* | 1/2008 | Asgeirsson | A61F 2/66 | 623/55 |
| 2008/0228288 A1* | 9/2008 | Nelson | A61F 2/66 | 623/55 |
| 2010/0042228 A1* | 2/2010 | Doddroe | A61F 2/66 | 623/55 |
| 2010/0298954 A1* | 11/2010 | Curtis | A61F 2/66 | 623/55 |
| 2011/0107581 A1* | 5/2011 | Williams | A61F 2/5044 | 29/428 |
| 2011/0320012 A1* | 12/2011 | Christensen | A61F 2/66 | 623/55 |
| 2013/0066439 A1* | 3/2013 | Zamora | A61F 2/66 | 623/55 |
| 2013/0123942 A1* | 5/2013 | Chen | A61F 2/66 | 623/53 |

* cited by examiner

ADDITIVE MANUFACTURING PRODUCED PROSTHETIC FOOT

CROSS-REFERENCE TO RELATED APPLICATIONS

This application is a divisional of U.S. patent application Ser. No. 14/214,842, filed on Mar. 15, 2014, which claims priority from U.S. Provisional Patent Application No. 61/801,118, filed on Mar. 15, 2013, which is incorporated by reference herein in its entirety.

BACKGROUND

Various types of prosthetic feet currently exist and would be familiar to those of skill in the art. Generally, it is desirable to produce prosthetic feet that absorb energy during heel strike, and transfer the energy to the toe of the foot as the amputee's gait cycle progresses. Ideally, this energy is released at the moment of toe-off to provide energy for the next step.

Active amputees who engage in sports or other strenuous physical activities typically require a prosthetic foot that is as efficient as possible at absorbing energy during heel strike and transferring the energy to the toe of the prosthetic foot for release at toe-off. Such prosthetic feet can be complex and expensive. Such prosthetic feet are also generally constructed from one or more spring-type plates that are connected by elastomeric or other materials and, therefore, do not typically resemble anything close to an actual human foot.

In contrast to active amputees, amputees that are more sedentary may not require or want a prosthetic foot with such substantial or efficient energy storage and/or energy transfer capabilities. Alternatively, active or sedentary amputees may sometimes simply prefer to wear a prosthesis with a more lifelike foot or a lighter foot, even if that foot is less effective at storing and transferring energy during the amputee's gait cycle. Further, some amputees may simply prefer a more cost effective prosthetic foot.

What is needed is a prosthetic foot that is easy to manufacture and is lower in cost than most prosthetic feet with high energy transfer efficiency.

SUMMARY

In one embodiment, a prosthetic foot is provided, the prosthetic foot comprising: a primary foot member extending from a heel portion to a toe portion of the foot; a shock absorbing heel member extending downward from an underside of the primary foot member; at least one tendon extending from the heel member and connecting to a more forward portion of the primary foot member; and a connecting element extending upward from a top surface of the heel portion of the primary foot member; wherein at least the primary foot member, the heel member, and at least one tendon are a unitary structure produced by an additive manufacturing process.

In another embodiment, a prosthetic foot is provided, the prosthetic foot comprising: a primary foot member extending from a heel portion to a toe portion of the foot; a shock absorbing heel member extending downward from an underside of the primary foot member; and at least one tendon extending from the heel member and connecting to a more forward portion of the primary foot member; wherein at least one of the primary foot member, the heel member, and at least one tendon are a unitary structure produced by an additive manufacturing process.

In another embodiment, a prosthetic foot is provided, the prosthetic foot comprising: a primary foot member extending from a heel portion to a toe portion of the foot; a shock absorbing heel member extending downward from an underside of the primary foot member; at least one tendon extending from the heel member and connecting to a more forward portion of the primary foot member; and a connecting element extending upward from a top surface of the heel portion of the primary foot member, the connecting element comprising a plurality of grouped rods surrounded by an elastomeric band; wherein at least the primary foot member, the heel member, at least one tendon, and the plurality of grouped rods are produced by an additive manufacturing process.

BRIEF DESCRIPTION OF THE DRAWINGS

The accompanying figures, which are incorporated in and constitute a part of the specification, illustrate various example apparatuses and systems, and are used merely to illustrate various example embodiments.

DETAILED DESCRIPTION

Embodiments of the prosthetic foot are directed to a lightweight and cost-effective prosthetic foot that is produced by an additive manufacturing process. One exemplary embodiment of such a prosthetic foot 5 is illustrated by the various views of FIGS. 1-7.

Additive manufacturing is a well-known technique for producing a variety of small and even large three dimensional objects, and is frequently utilized in rapid prototyping and rapid manufacturing applications. The objects created by an additive manufacturing process can be quite complex, even including objects trapped but freely moving within other objects.

Figure 1:
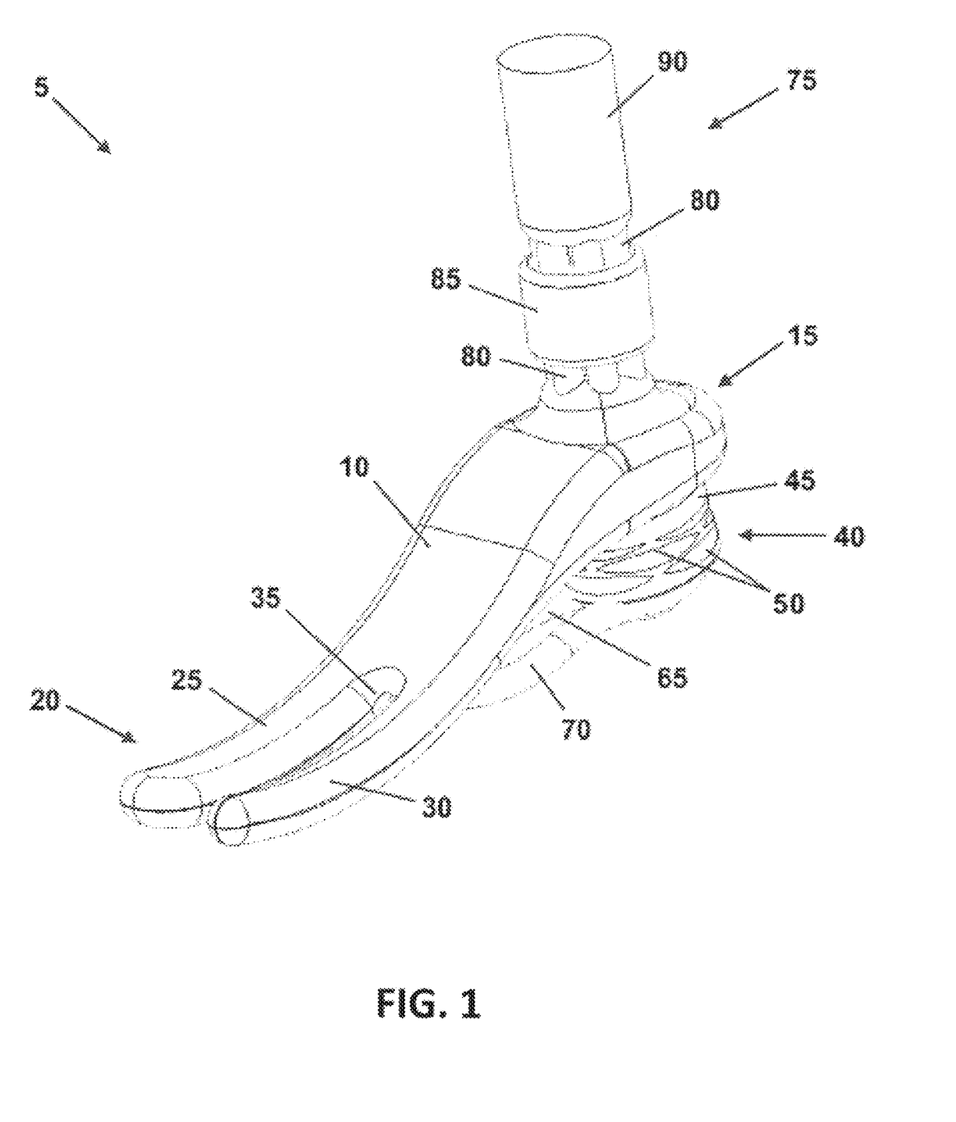
FIG. 1 illustrates a perspective view of an exemplary embodiment of a prosthetic foot.
Figure 2:
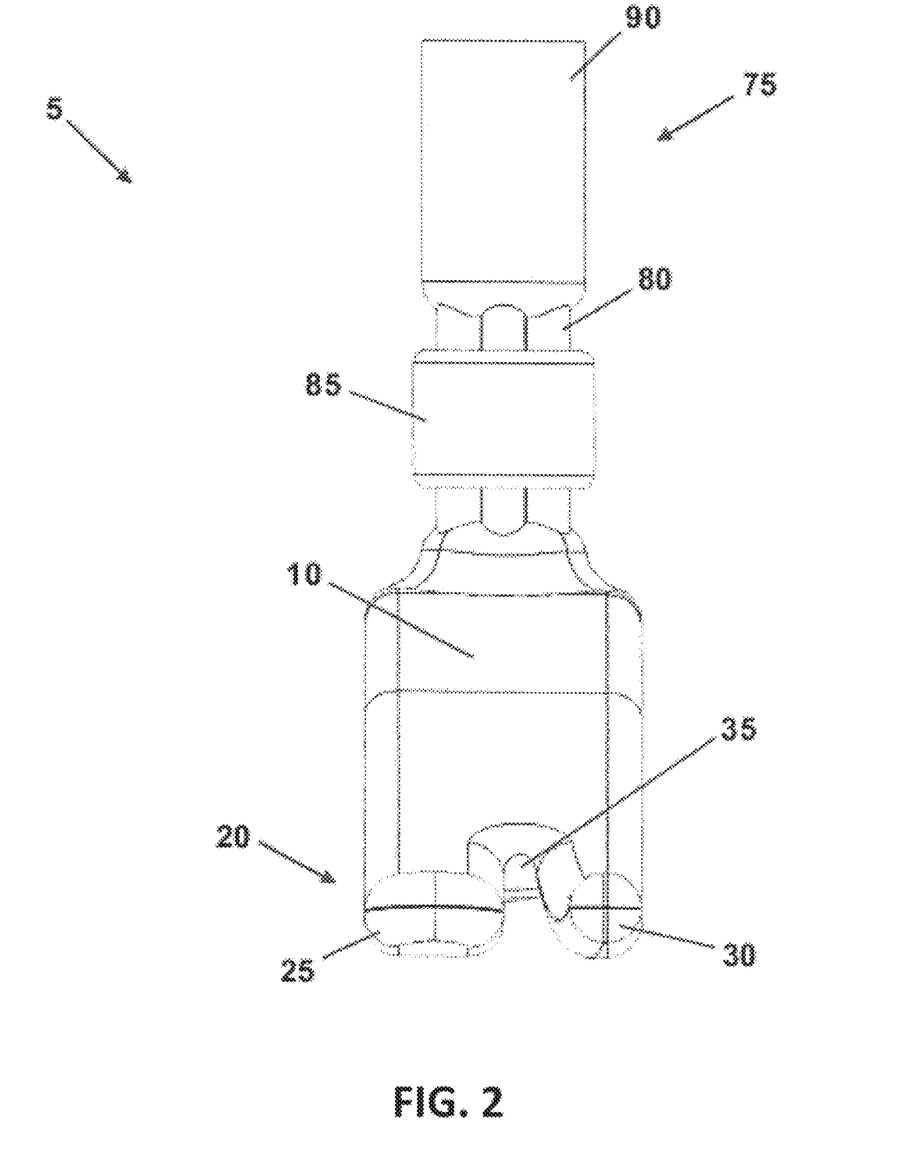
FIG. 2 illustrates a front elevational view of an exemplary embodiment of a prosthetic foot.
Figure 3:
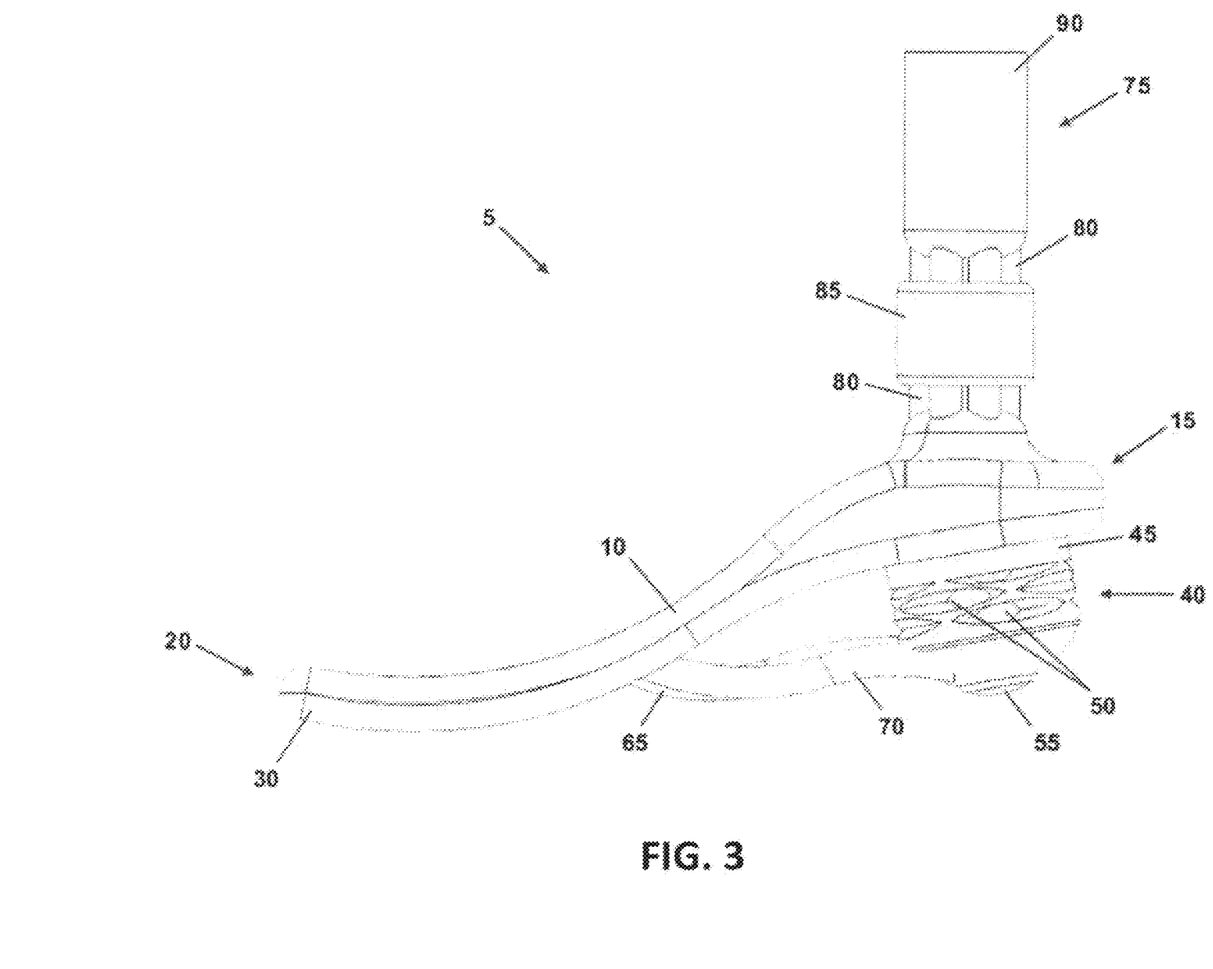
FIG. 3 illustrates a left elevational view of an exemplary embodiment of a prosthetic foot.
Figure 4:
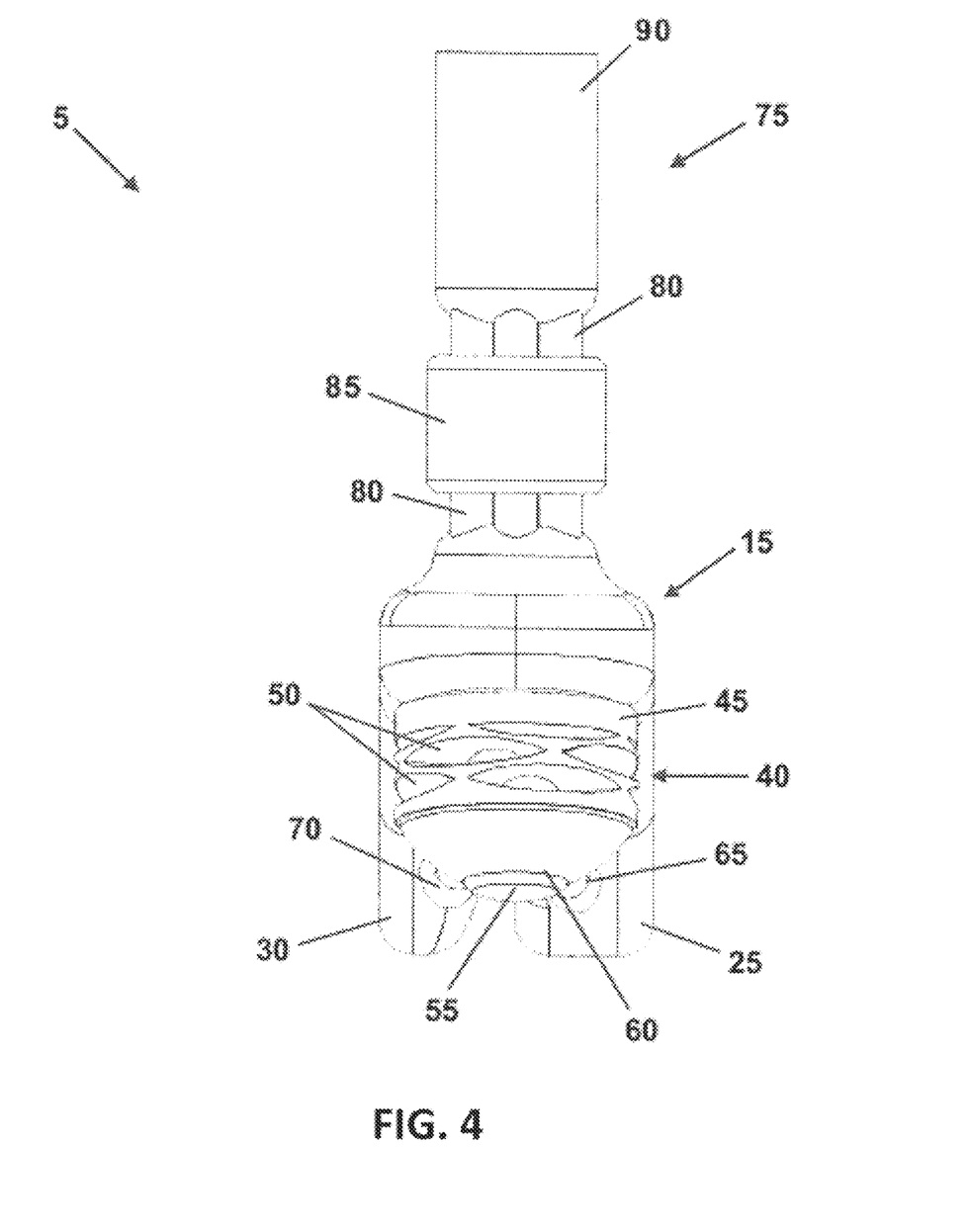
FIG. 4 illustrates a rear elevational view of an exemplary embodiment of a prosthetic foot.
Figure 5:
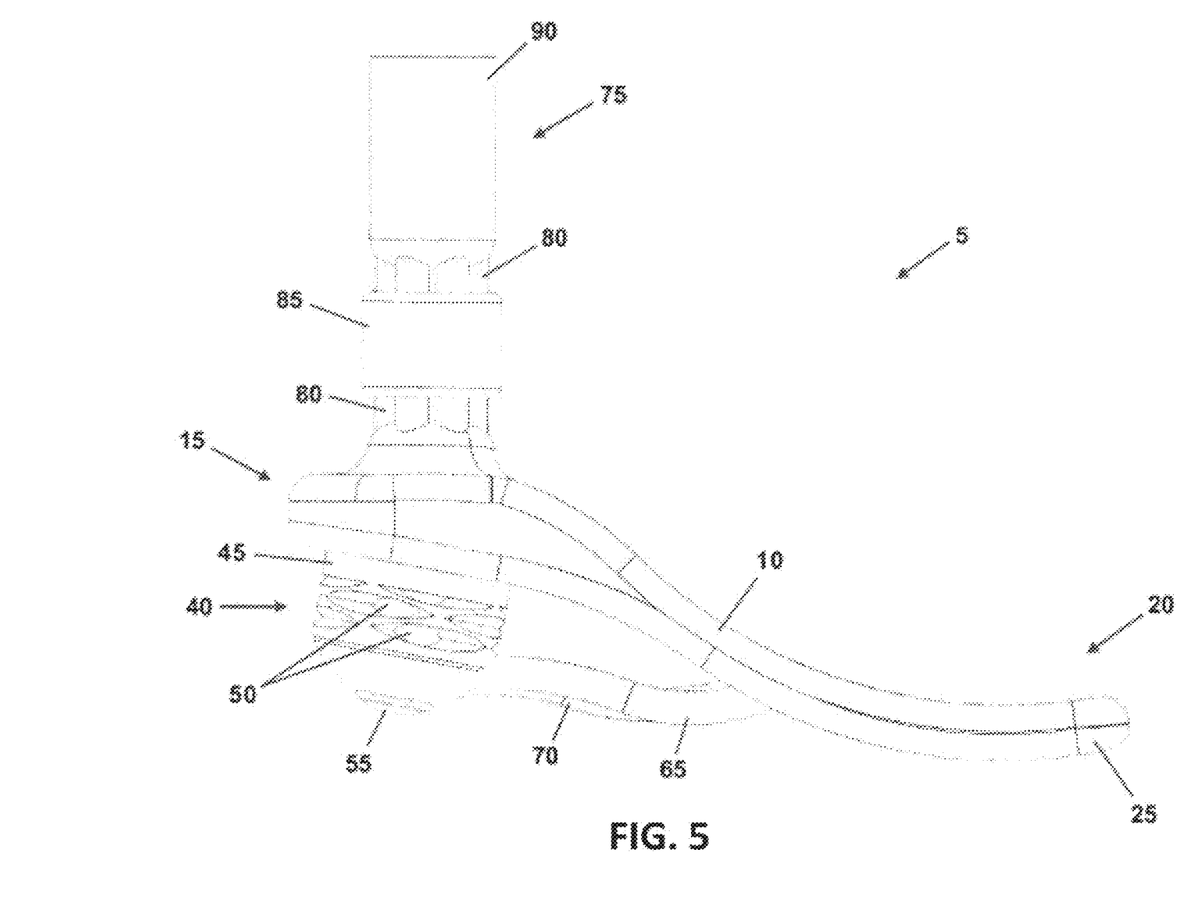
FIG. 5 illustrates a right elevational view of an exemplary embodiment of a prosthetic foot.
Figure 6:
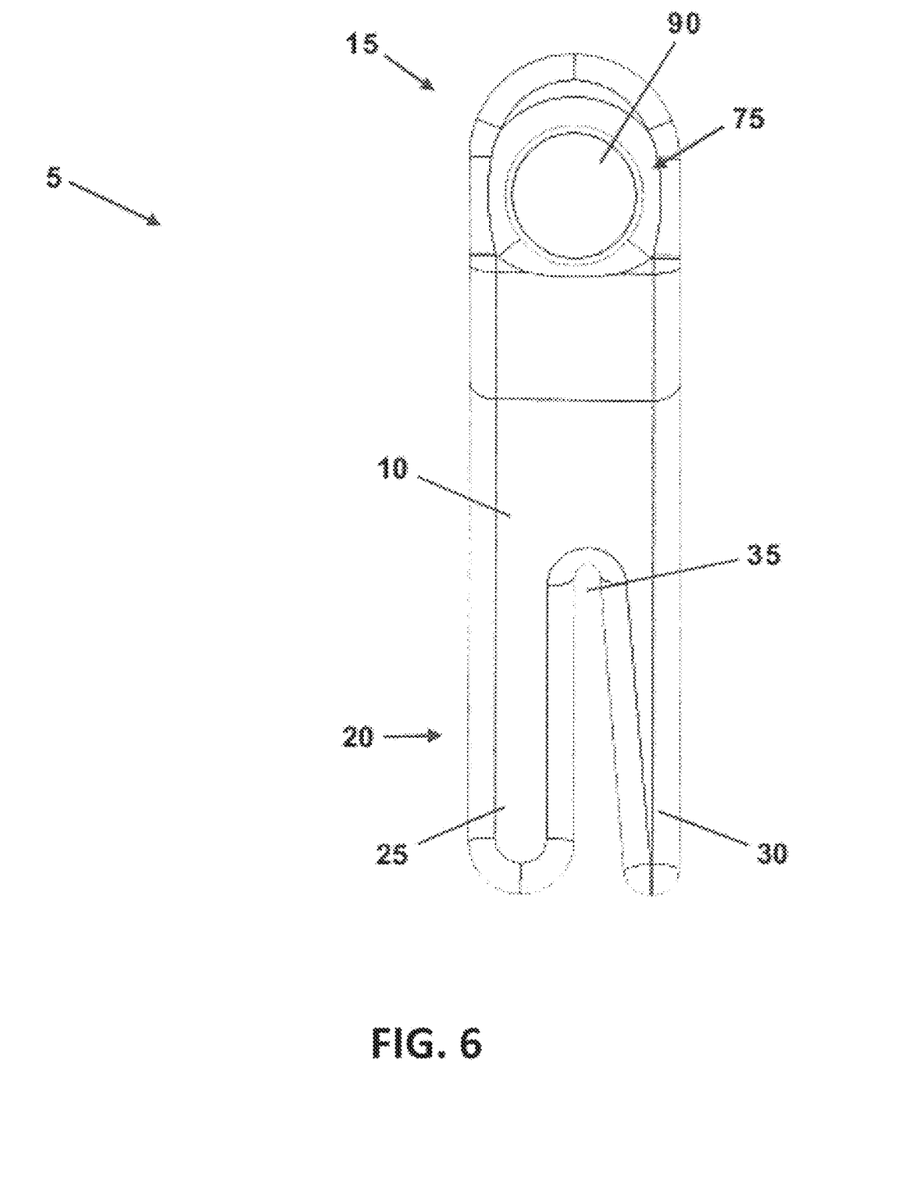
FIG. 6 illustrates a top elevational view of an exemplary embodiment of a prosthetic foot.

There are different types of additive manufacturing processes including, without limitation, stereo lithography (SLA), digital light processing (DLP), 3D printing, selective laser sintering (SLS), selective heat sintering (SHS), direct metal laser sintering (DMLS), electron beam melting (EBM), and fused deposition modeling (FDM). These various additive manufacturing processes collectively permit complex 3-D objects to be produced from numerous materials including, for example, photopolymers, paper, metals and metal alloys, plastics, and even edible materials. Regardless of the particular additive manufacturing process selected, however, additive manufacturing differs from typical machining processes in that additive manufacturing operates to produce a buildup of material rather than to remove material FIG. 1 illustrates a perspective view of a prosthetic foot 5. Prosthetic foot 5 may be configured for use by a human amputee. Prosthetic foot 5 may be constructed using an additive manufacturing process. FIGS. 1-7 illustrate various views of prosthetic foot 5.

An additive manufacturing process produced prosthetic foot 5 may include a primary foot member 10 that generally extends in length from a heel portion 15 to a toe portion 20. Heel portion 15 of primary foot member 10 may be thicker than toe portion 20, such that primary foot member 10 tapers from heel portion 15 to toe portion 20.

Primary foot member 10 may be contoured such that there is a downward slope when moving from heel portion 15 toward toe portion 20. This contour may be selected, for example, to substantially mimic the arch of a human foot. Primary foot member 10 may be contoured around the edges, in toe portion 20, or in other areas to replicate a human foot. Prosthetic foot 5 may be provided with a reduced top line in comparison to known prosthetic feet. This reduced top line may facilitate the donning and doffing of a shoe.

Toe portion 20 of primary foot member 10 may be split for enhanced stability. Toe portion 20 of primary foot member 10 may be split to better control energy release at toe-off. In one embodiment, toe portion 20 of primary foot member 10 is split into two toe sections 25, 30. One of two toe sections 25, 30 may be larger than the other. Toe portion 20 of other embodiments of primary foot member 10 may be split into a different number of toe sections and/or may be shaped to more closely mimic a human foot.

Toe sections 25, 30 may be separated by a gap 35. The size of gap 35 between toe sections 25, 30 may vary. In one embodiment, one or more connecting bands (not shown) may pass from one toe section 25 to the other toe section 30, spanning gap 35 therebetween. Such connecting bands (not shown) may be used to limit deflection of toe portion 20 and/or toe sections 25, 30. The connecting bands (not shown) may facilitate foot contact and stability.

A heel member 40 may extend downward from the underside of primary foot member 10. Heel member 40 may have a number of shapes and may be of various sizes. In one embodiment, heel member 40 may be substantially cylindrical in shape and may have a largely hollow interior that is bounded by a closed sidewall 45 of some thickness. A plurality of apertures 50 may pass through sidewall 45. Apertures 50 may enhance the compressibility and shock absorbing characteristics of heel member 40. Apertures 50 may take on any of a variety of shapes, and more than one shape may be present in a given heel member 40.

Heel member 40 may be formed as a hollow element having a wall in the form of a gapped spiraling or helical coil having an upper and lower terminus. That is, heel member 40 may resemble a partially uncoiled spring. The wall of heel member 40 may be similarly segmented to produce gapped vertical or angled cords or bands which, in some embodiments, may crisscross. Other designs are also possible, as long as the resulting heel member 40 is imparted with satisfactory shock absorbing characteristics.

The shock absorbing properties of heel member 40, and other heel member embodiments, may be further controlled by the introduction thereto of an additional elastomeric element(s). In one embodiment, heel member 40 may include an additional elastomeric element in the form of a bumper 55 (as illustrated in FIGS. 3-5 and 7) that may be inserted into the interior of heel member 40 via an opening 60 located in the underside of heel member 40. A lower end of bumper 55 may protrude slightly from the bottom of heel member 55 is fully inserted thereto, such that bumper 55 may contribute to the shock absorbing characteristics of heel member 40 upon heel strike. Bumper 55 may protrude slightly from the bottom of heel member 40 and may contribute to the energy transfer characteristics of heel member 40 between heel strike and toe-off.

Figure 7:
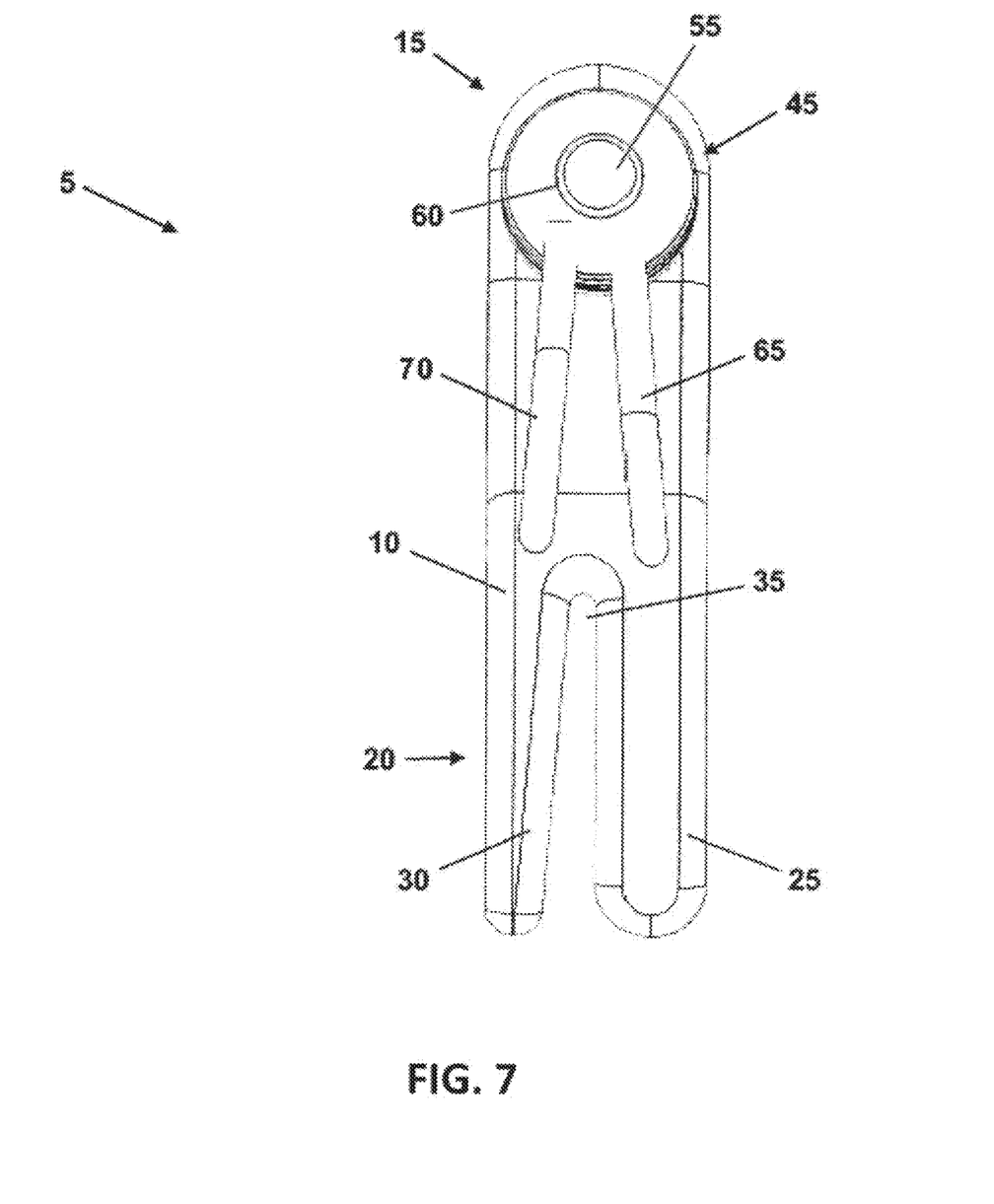
FIG. 7 illustrates a bottom elevational view of an exemplary embodiment of a prosthetic foot.

A pair of tendons 65, 70 are shown to extend forward from heel member 40 and to connect with a more forward portion of primary foot member 10. In one embodiment, as can be best observed in FIG. 7, tendons 65, 70 may connect with primary foot member 10 at a point just rearward of split toe sections 25, 30. As illustrated in FIG. 7, one tendon 65 may be associated with one toe section 25, and the other tendon 70 may be associated with the other toe section 30. Tendons of other embodiments may connect to the associated primary foot member 10 at other locations thereon.

Tendons 65, 70 are illustrated as having a substantially circular cross-sectional shape and having a particular contour. However, other tendons of other prosthetic foot embodiments may have other cross-sectional shapes and contours. In any case, tendons 65, 70 may be used to, for example, facilitate stability during ambulation by tying heel portion 15 of foot 5 to toe portion 20, to limit toe deflection, and/or to produce a slightly earlier start to the plantar flexion stage of foot motion.

A connecting element 75 extends upward from a top surface of heel portion 15 of primary foot member 10. Unlike the remainder of prosthetic foot 5, connecting element 75 may not be produced during the additive manufacturing process. Rather, connecting element 75 may be a separate component that is connected to primary foot member 10 subsequent to the additive manufacturing thereof.

Connecting element 75 may function as an ankle to connect prosthetic foot 5 to the remainder of a prosthetic leg. Connecting element 75 may include a number of individual rods 80 that are grouped together to form a torsional pylon. Rods 80 may be of various cross-sectional shape, but are shown to be of substantially round cross-section in this exemplary embodiment.

Rods 80 may each be connected at one end to primary foot member 10. The size, number, and stiffness of rods 80 may be controlled in order to likewise control the stiffness of the torsional pylon (ankle). Flexion of the pylon may be further controlled by providing an elastomeric band 85 that encircles the group of rods 80. The stiffness of elastomeric band 85 used may vary in order to provide greater control over pylon (ankle) stiffness. A proximal (free) end of rods 80 may be collected in a housing 90 or a similar element that facilitates connection of the pylon to a corresponding connecting element of a prosthetic leg.

It should be understood that the entirety of prosthetic foot 5, except for the connecting element 75, may be produced as a unitary structure via use of an additive manufacturing process. In another embodiment, it is possible to form connecting element 75 by means of the additive manufacturing process. In another embodiment, at least one of primary foot member 10, heel member 40, and tendons 65, 70 are a unitary structure produced by an additive manufacturing process.

The prosthetic foot 5, absent connecting element 75, may be produced by any of various possible additive manufacturing processes. Prosthetic foot 5 may be manufactured from a plastic material (e.g., nylon) using a selective laser sintering (SLS) additive manufacturing process.

The use of an additive manufacturing process facilitates the production of custom prosthetic feet. For example, an amputee's existing foot could be scanned and mirrored and then used as a model for an additive manufacturing produced prosthetic foot. Alternatively, various off-the-shelf (i.e., non-custom) prosthetic feet could be produced with a given foot covering some range of shoe sizes (e.g., size 6-8, size 9-11, etc.). Still alternatively, a different foot could be produced for each shoe size while still being an off-the-shelf foot. Still further, it is also possible to produce a prosthetic foot whose length may be reduced by easily trimming away material to produce a foot of given shoe size. Such a foot may have trimming indications for this purpose.

Figure 8:
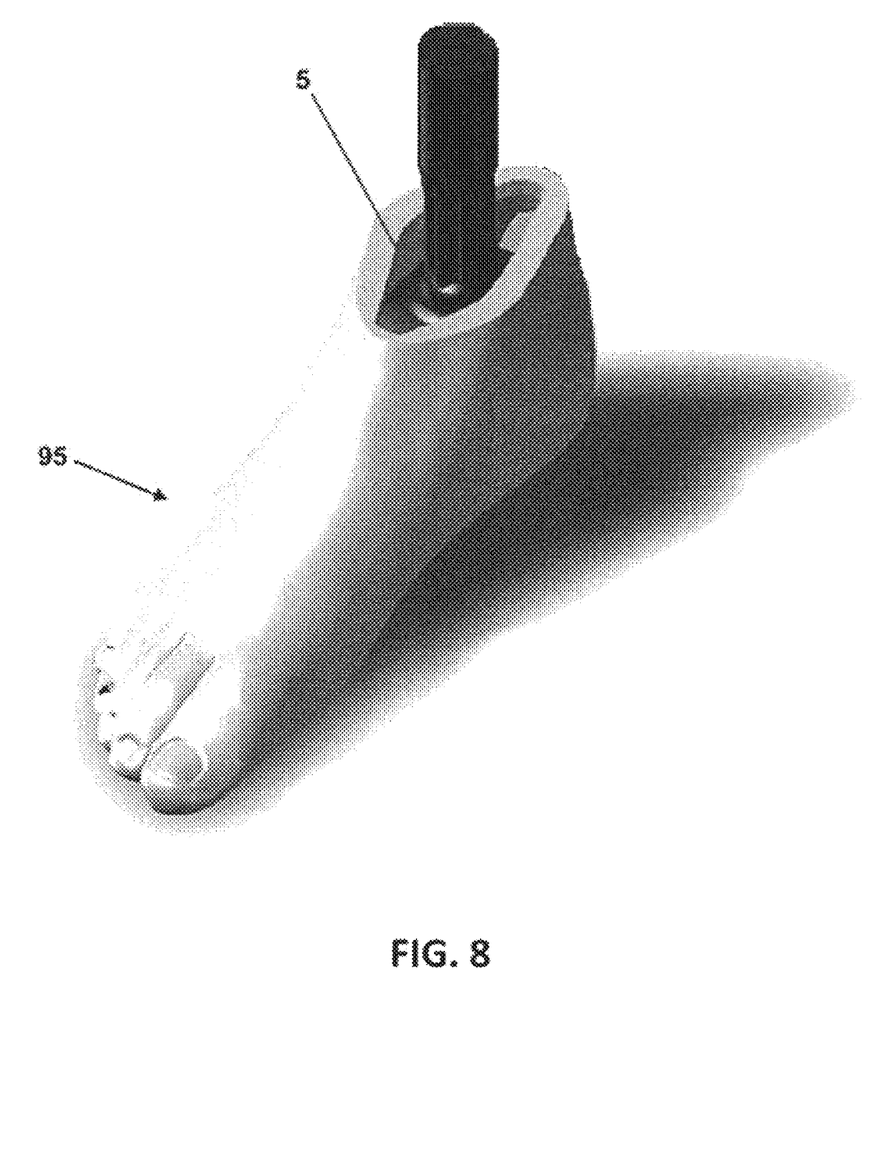
FIG. 8 illustrates a perspective view of an exemplary embodiment of a prosthetic foot inserted into a hollow cosmetic foot shell.

As illustrated in FIG. 8, a separate hollow foot shell 95 may be placed on, over, or otherwise connected to, the additive manufacturing produced portion of prosthetic foot 5 to create a multi-piece prosthetic foot with a further improved cosmetic appearance. In one embodiment, by means of for example a 3-D printing process a prosthetic foot may be produced as described above within an outer foot shell that is more anatomically correct. The foot shell in such an embodiment may be only minimally connected to the internal foot structure so as to keep the foot shell in place thereon.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A prosthetic foot structure, comprising:
a primary foot member having a heel portion, a toe portion with a pair of toe sections separated by a gap, and an elongated intermediate portion configured as an arch extending downward from the heel portion toward the toe portion; and
a heel member including a hollow cylindrical spring wall extending downward from the heel portion of the primary foot member;
wherein the spring wall has apertures reaching through the spring wall, the apertures are elongated around the circumference of the spring wall and arranged in rows reaching fully around the spring wall, and the apertures in each row are circumferentially staggered relative to the apertures in an adjacent row; and
wherein the primary foot member and the heel member are portions of a unitary body of material formed by additive manufacturing.

2. The prosthetic foot structure of claim 1, wherein the heel member further includes a lower end wall with an opening, and further comprising an elastomeric bumper that is separate from the unitary body of material and installed in the opening.

3. The prosthetic foot structure of claim 1, further comprising a pair of elongated portions of the unitary body of material extending forward from the heel member to the primary foot member.

* * * * *